US00PP23482P2

(12) United States Plant Patent
Probst

(10) Patent No.: US PP23,482 P2
(45) Date of Patent: Mar. 19, 2013

(54) ***PHYSOSTEGIA* PLANT NAMED 'PINK MANNERS'**

(50) Latin Name: *Physostegia virginiana*
Varietal Denomination: Pink Manners

(76) Inventor: Darrell R. Probst, Hubbardston, MA (US)

( * ) Notice: Subject to any disclaimer, the term of this patent is extended or adjusted under 35 U.S.C. 154(b) by 134 days.

(21) Appl. No.: 13/135,166

(22) Filed: Jun. 28, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Kent L Bell
(74) *Attorney, Agent, or Firm* — Penny J. Aguirre

(57) ABSTRACT

A new cultivar of *Physostegia* plant, 'Pink Manners', characterized by its flowers that are light rose pink in color, its clump-forming growth habit due to its very short rhizomes, and its mature height of 76 to 107 cm.

2 Drawing Sheets

Botanical classification: *Physostegia virginiana.*
Variety denomination: 'Pink Manners'.

BACKGROUND OF THE INVENTION

The present invention relates to a new and distinct cultivar of Obedient Plant, botanically known as *Physostegia virginiana* 'Pink Manners' and will be referred to hereinafter by its cultivar name, 'Pink Manners'. The new cultivar of *Physostegia* is a hardy herbaceous perennial grown for landscape use.

The new cultivar was developed through a breeding program conducted by the inventor in Hubbardston, Mass. The goal was to produce a cultivar of *Physostegia* that produced pink flowers and exhibited a clump-forming growth habit that lacked the spreading growth habit by long rhizomes that is typical of cultivars of pink flowering *Physostegia.*

'Pink Manners' arose from a cross made in August of 2005 between unnamed advanced generation plants from the inventor's breeding program as both the female and male parents. 'Pink Manners' was selected as a single unique plant in July of 2008.

Asexual reproduction of the new cultivar was first accomplished by division in October of 2008 by the inventor in Hubbardston, Mass. It has been determined that the characteristics are stable and reproduced true to type in successive generations.

SUMMARY OF THE INVENTION

The following traits have been repeatedly observed and are determined to be the characteristics of the new cultivar. These attributes in combination distinguish 'Pink Manners' as a unique cultivar of *Physostegia.*

1. 'Pink Manners' exhibits flowers that are light rose pink in color.
2. 'Pink Manners' exhibits a clump-forming growth habit.
3. 'Pink Manners' exhibits very short rhizomes.
4. 'Pink Manners' attains a height of 76 to 107 cm (30 to 42 inches).

'Pink Manners' can be compared to its parent plants. The female parent is similar to 'Pink Manners' in having flowers that are pink in color, but differs from 'Pink Manners' in having long rhizomes and therefore lacking a clump-forming plant habit. The male parent is similar to 'Pink Manners' in having very short rhizomes and a clump-forming plant habit, but differs from 'Pink Manners' in having flowers that are white in color. 'Pink Manners' can also be compared to the cultivars 'Miss Manners' (U.S. Plant Pat. No. 12,637) and 'Rosea' (not patented). 'Miss Manners' is similar to 'Pink Manners' in having a clump-forming growth habit, but differs from 'Pink Manners' in having flowers that are white in color and in being shorter in height. 'Rosea' is similar to 'Pink Manners' in plant height and in having flowers that are light rose pink in color, but differs from 'Pink Manners' in having long rhizomes with a spreading growth habit.

BRIEF DESCRIPTION OF THE DRAWINGS

The accompanying colored photographs illustrate the overall appearance and distinct characteristics of the new *Physostegia.*

The plant depicted in FIG. 1 is about one year in age as grown outdoors in a one-gallon container in Kensington, Conn. and provides a close-up view of the inflorescences of 'Pink Manners'.

Figure 1:
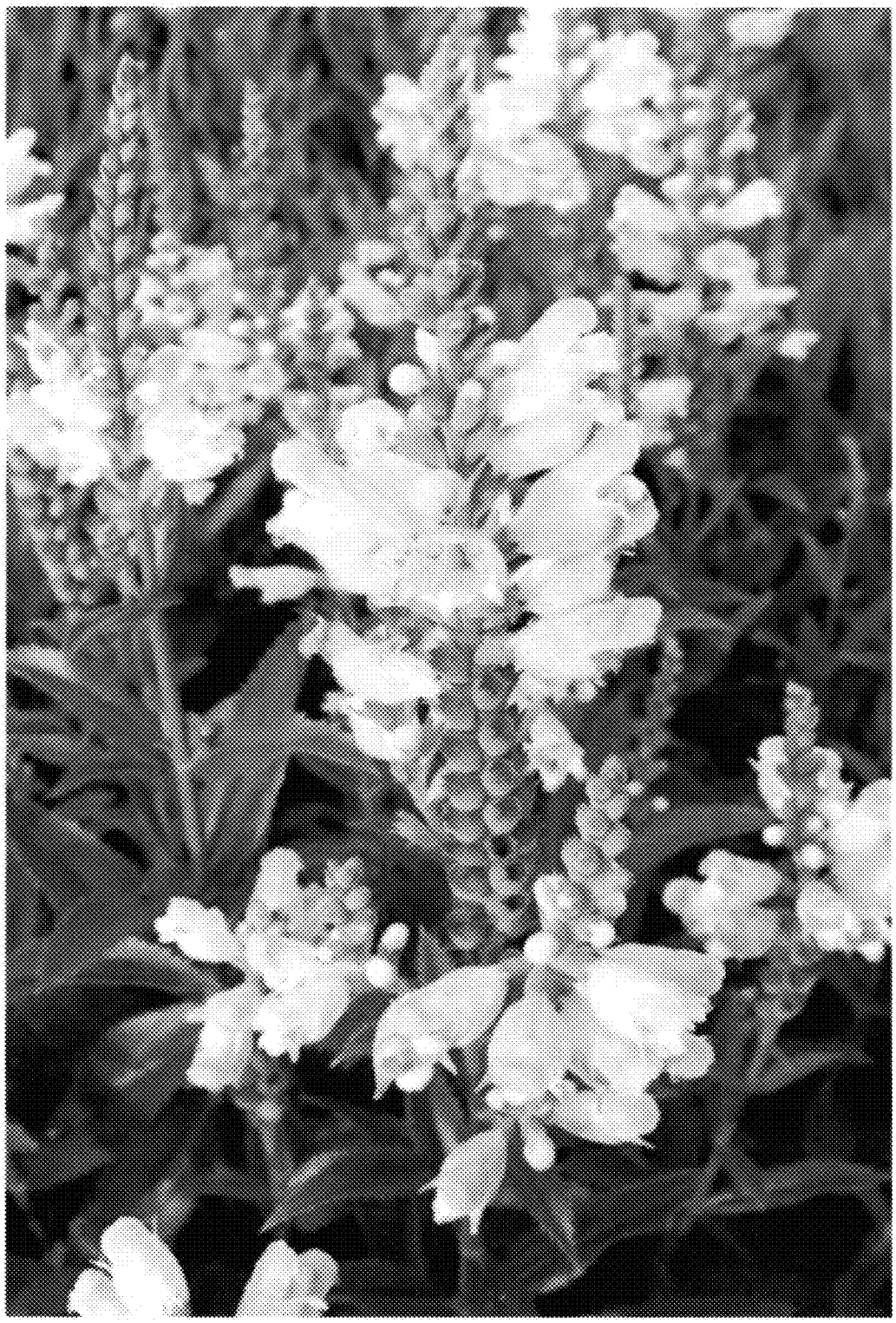
Figure 2:
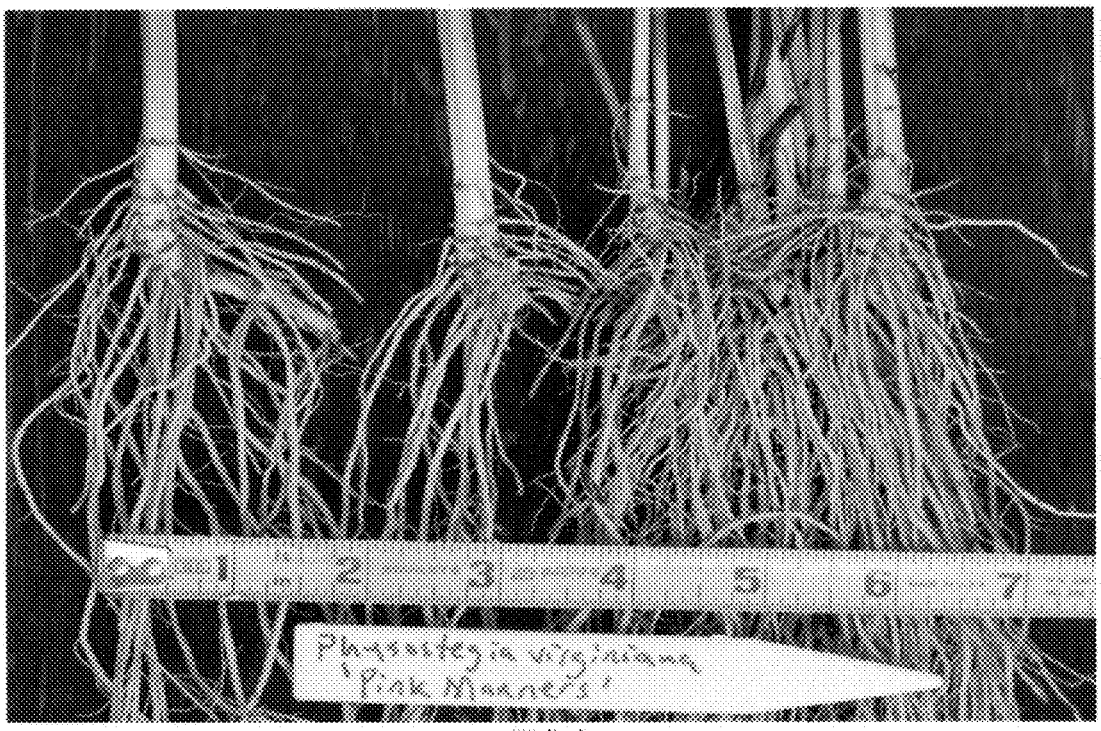

The plant in the photograph in FIG. 2 was about one year in age from a division as grown in a garden in Hubbardston, Mass. and illustrates the rhizomes on current season's stems still attached to the old (dead) stems.

Figure 3:
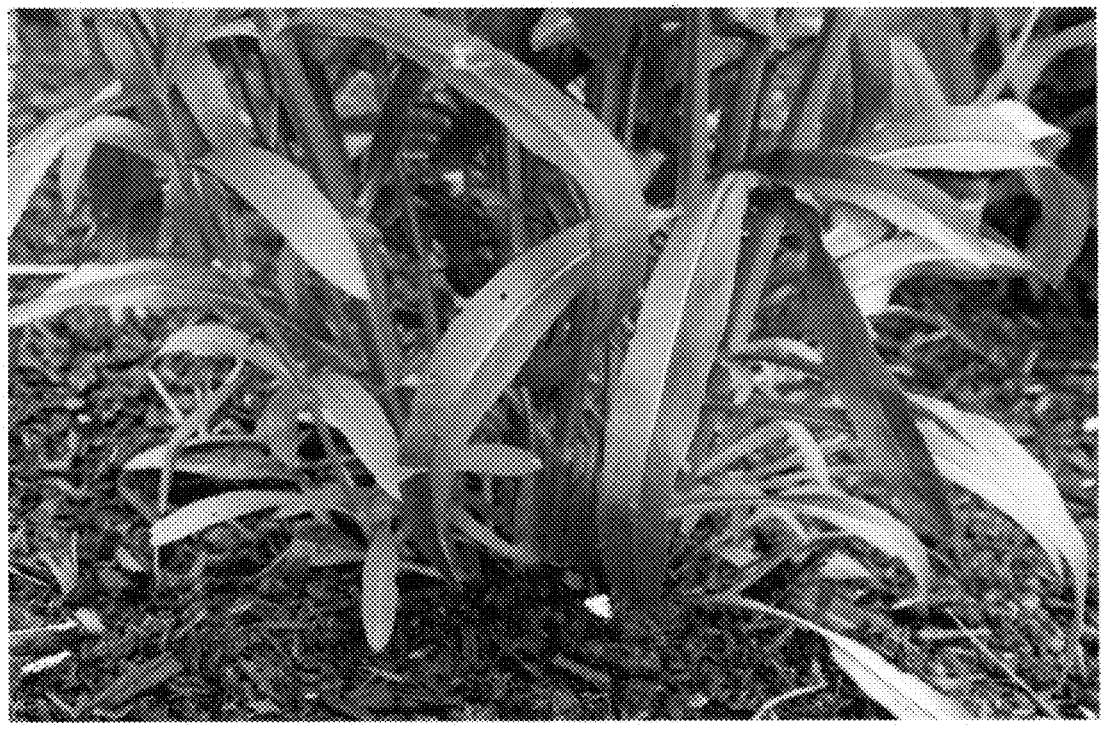

The plant depicted in FIG. 3 is about 18 months in age as grown in New Hope, Minn. and illustrates the clump forming growth habit of 'Pink Manners'. The colors in the photograph may differ slightly from the color values cited in the detailed botanical description, which accurately describe the colors of the new *Physotegia.*

DETAILED BOTANICAL DESCRIPTION

The following is a detailed description of two year-old plants of the new cultivar as grown outdoors in a garden in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—3 to 6 weeks in mid to late summer.

*Plant habit*.—Clump-forming with short rhizomes, upright.

*Height and spread*.—Matures to 76 to 107 cm in height and 38 to 61 cm in width.

*Hardiness*.—At least in U.S.D.A. Zones 4 to 9.

*Diseases and pests*.—No susceptibility or resistance to diseases or pests has been observed.

*Root description*.—Fleshy.

*Rhizomes*.—Very short, range from 1.5 to 5 cm in length, slightly longer lengths may be observed in overly fertile soils, range of 3 to 4 mm in width, a blend of 161D and 155B in color.

*Propagation*.—Terminal stem cutting, division.

*Growth rate*.—Moderate.

Stem description (flowering):

*Shape*.—Square.

*Stem color*.—A blend of 143A to 138A.

*Stem size*.—Average of 5 mm in diameter and 50 cm in length.

*Stem surface*.—Glabrous, satiny.

*Branching habit*.—Basal branching only.

*Stem quantity*.—Average of 20 per plant 2 years in age.

Foliage description:

*Leaf division*.—Simple.

*Leaf arrangement*.—Opposite.

*Leaf shape*.—Narrowly elliptic to slightly lanceolate.

*Leaf size*.—An average of 15 cm in length and 3 cm in width when mature.

*Leaf number*.—Average of 20 per stem.

*Leaf base*.—Cuneate.

*Leaf apex*.—Acute.

*Leaf margin*.—Serrate.

*Leaf venation*.—Pinnate, upper surface mid rib 138A in color, lower surface mid rib 138B in color.

*Leaf surface*.—Glabrous, satiny sheen on upper and lower surface.

*Leaf internode length*.—An average of 5.2 cm.

*Leaf color*.—Young and mature leaves upper surface 137A, young and mature leaves lower surface 138A.

*Leaf attachment*.—Sessile.

*Foliage fragrance*.—None.

Flower description:

*Inflorescence type*.—Terminal and axillary spikes of bilabiate flowers.

*Lastingness of inflorescence*.—Individual flowers last 2 to 3 days, spikes bloom for about 2 weeks.

*Inflorescence size*.—An average of 15 cm in length and 3.5 cm in diameter.

*Flower type*.—Zygomorphic, sympetalous, bilabiate, perfect.

*Flower arrangement*.—2-ranked to whorled, flowers closely held on terminal and axillary spikes.

*Flower number*.—An average of 45 flowers per terminal spike and 28 per axillary spike, an average of 7 spikes per stem.

*Flower fragrance*.—None.

*Flower buds*.—Obovate in shape, an average of 5 mm in length and 3 mm in width, surface is glabrous, color a blend of 138B and 138C.

*Flower size*.—About 1.5 cm in depth and about 1 cm in diameter.

*Peduncles*.—About 1 cm in length and 2 mm in diameter, glabrous, 138A in color.

*Rachis*.—An average of 15 cm in length, 2 mm in diameter, 138A in color.

*Pedicels*.—None, flowers sessile to peduncle.

*Bracts*.—1 per flower, lanceolate in shape, an average of 5 mm in length and 2 mm in width, glabrous surface, cuneate base, acute apex, 138B in color.

*Calyx*.—5-sepals fused on lower ¾, tubular campanulate in shape, with sharp-tipped, short triangular teeth, about 7 mm in length and 4 mm in width, persistent.

*Sepals*.—5, primarily fused with un-fused tips, lanceolate in shape and about 1.5 mm in width and 7 mm in length, 138B in color, surface is glabrous, fused base, aristate apex, entire margins.

*Petals*.—Fused base with un-fused portion spreading and 2-lipped, lower lip; broadly obovate in shape, base is truncate to tube, single-lobed with rounded apex, margin is entire, about 1.5 cm in depth and 1 cm in diameter, color of upper surface NN155A suffused with a blend of 76A and 76B, color of lower surface is NN155A suffused with 76B and speckled with N80A on the lower lip, upper lip; ovate in shape, rounded apex, base truncate to tube, margin is entire, about 6 mm in length and 4 mm in width, tube portion; about 1 cm in length and 4 mm in width, color NN155A, all surfaces glabrous, color of all petals fade to 161D.

Reproductive organs:

*Gynoecium*.—1 Pistil, style is about 1.3 cm in length, 0.3 mm in width and NN155D in color, stigma is bi-fid, about 0.3 mm in diameter and 155A in color, ovary is superior, about 0.5 mm in diameter, translucent and 195D in color.

*Androecium*.—4 stamens, filament is about 9 mm in length, adnate to corolla and NN155D in color, anthers are globose in shape, about 0.7 mm in diameter, dorsifixed, and 177A in color, pollen is moderate in abundance and 162C in color.

*Fruit*.—Four per flower, 3-angled nutlets, 3 to 4 mm in length, 1.5 to 2 mm in width, glabrous, 145B in color tinged 183D in the center when newly formed, 200A in color when mature.

It is claimed:

1. A new and distinct variety of *Physostegia* plant named 'Pink Manners' as described and illustrated herein.

* * * * *